United States Patent
Barrows

(10) Patent No.: US 6,371,612 B2
(45) Date of Patent: Apr. 16, 2002

(54) CLIP-IN LASER EYEWEAR ASSEMBLY

(76) Inventor: Thomas D. Barrows, 6826 Hemlock La., Maple Grove, MN (US) 55369

(*) Notice: Subject to any disclaimer, the term of this patent is extended or adjusted under 35 U.S.C. 154(b) by 0 days.

(21) Appl. No.: 09/793,943

(22) Filed: Feb. 27, 2001

Related U.S. Application Data

(60) Provisional application No. 60/185,950, filed on Feb. 29, 2000.

(51) Int. Cl.[7] .................... G02C 9/00; G02C 7/08; G02C 5/04
(52) U.S. Cl. .................... 351/48; 351/47; 351/128
(58) Field of Search .................... 351/47, 48, 57, 351/58, 44, 41, 128

(56) References Cited

U.S. PATENT DOCUMENTS 5,917,574 A * 6/1999 Chang .................... 351/47
6,234,628 B1 * 5/2000 Friedman .................... 351/48

* cited by examiner

Primary Examiner—Hung Xuan Dang
(74) Attorney, Agent, or Firm—Anthony G. Eggink

(57) ABSTRACT

An adjustable clip-in laser eyewear assembly for securement to the inside of a pair of eyeglasses. The eyewear assembly has a frame structure having a pair of filter lens frame members that are joined at the top by a brow bar structure having a spring member. Hooked clips are fixed and positioned at the top and exterior sides of each filter lens frame member. The hooked clips face outward from the laser eyewear assembly to position the assembly on the inside of the eyeglasses. The top and side clips in cooperation with the spring of the brow bar structure permit the adjustable securement of the laser eyewear assembly to the inside of the eyeglasses.

16 Claims, 2 Drawing Sheets

CLIP-IN LASER EYEWEAR ASSEMBLY

This application claims the benefit of U.S. Provisional Application No. 60/185,950 filed on Feb. 29, 2000.

BACKGROUND OF THE INVENTION

This invention relates generally to laser eyewear and particularly to a clip-in laser eyewear assembly for securement to the inside of a pair of eyeglasses. Particularly, the invention relates to an adjustable clip-in laser eyewear assembly which is constructed and arranged for securement to the inside of eyeglasses.

The use of lasers has become increasingly common, particularly, in the dental and medical arts. To protect the eyes of the user of the laser device, protective eyewear is recommended and required. Typically, the physician or dentist wears eyewear with magnifying loupes when working with lasers. These eyewear structures make it difficult to provide protective eyewear, i.e., laser filters. Because the magnifying loupes are positioned in front of the eyeglass lenses it is necessary to position the laser filter lenses against the back or on the inside of the eyeglasses.

Although the prior art has taught the use of utilizing various filter lenses for use with eyeglasses, i.e., clips used for sunglasses, the eyeglasses used in the medical and dental arts, for example, present unique difficulties, because of the magnifying loupes positioned in front of the eyeglass lenses. One prior art device (U.S. Pat. No. 5,917,574) teaches the use of an eyewear protection accessory which is positioned with respect to the inside and top of each lens frame member of the eyeglasses with magnifying loupes. The inside edge of the accessory lens frame is designed to be captured between the nosepiece of the eyeglasses and the back surface of the lens. This accessory structure, however, has limitations in its use, because the eyeglasses must be constructed and arranged to receive the inside edge of the accessory.

The clip-in laser eyewear assembly of the present invention provides an improvement and overcomes the difficulties of the prior art by providing a clip-in laser eyewear assembly that is constructed and arranged for positioning with respect to the outside and top of each lens frame member of the eyeglasses with magnifying loupes. An adjustable brow bar having a spring provides an internally directed force to secure the laser filter lens frames to the inside of the eyeglasses and further provides adjustability to accommodate different sized eyeglasses.

SUMMARY OF THE INVENTION

The clip-in laser eyewear assembly of the present invention is comprised of a clip-in structure comprised of a frame structure having a pair of lens frame members having laser filter lenses. The lens frame members are joined at the top by a brow bar structure having a spring member which provides an lateral internally directed force to secure the laser eyewear assembly to the inside of the eyeglass frame. Hooked clips are fixed and positioned at the top and exterior sides of each filter lens frame member. The exterior clips are constructed and arranged to engage the exterior sides of the eyeglass frame having the magnifying loupes. The top clips are constructed and arranged to engage the top of the eyeglass frame. Importantly, a spring member is positioned in the brow bar assembly or connecting structure between the filter lens frame members of the clip-in laser eyewear assembly. The spring member provides the clip-in laser eyewear with adjustment means to enable the clip-in structure assembly to be used with a range of eyeglass sizes. Further, the spring member provides an internally directed lateral force to the exterior clips to secure the clip-in structure to the eyewear with magnifying loupes.

These and other benefits of this invention will become clear from the following description by reference to the drawings.

DESCRIPTION OF THE PREFERRED EMBODIMENTS

The clip-in laser eyewear assembly 10 of the present invention is constructed and arranged to be worn with eyeglasses having magnifying loupes when working with laser equipment, such as by physicians and dentists. The protective lenses in the clip-in laser eyewear assembly 10 are comprised of laser filter lenses which are for use with Diode, Erbium, YAG, Argon, KTP, Ruby, Alexandrite and other laser sources.

Figure 1:
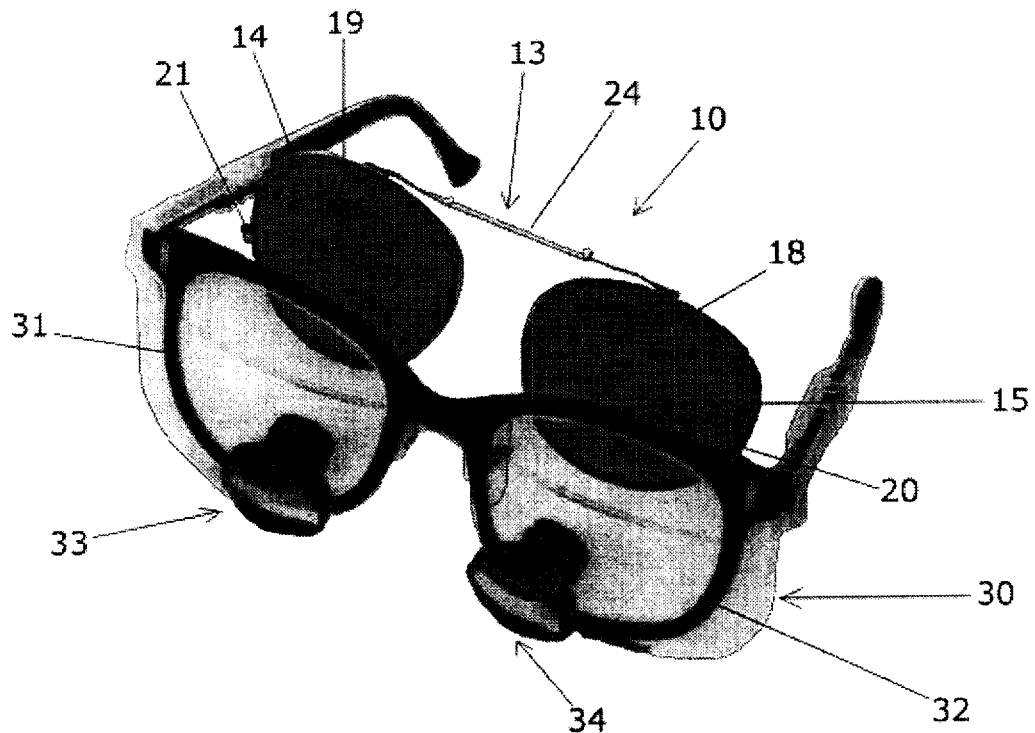
FIG. 1 is a perspective view showing the clip-in laser eyewear assembly of the invention positioned for securement on the inside of eyeglasses with magnifying loupes.
Figure 2:
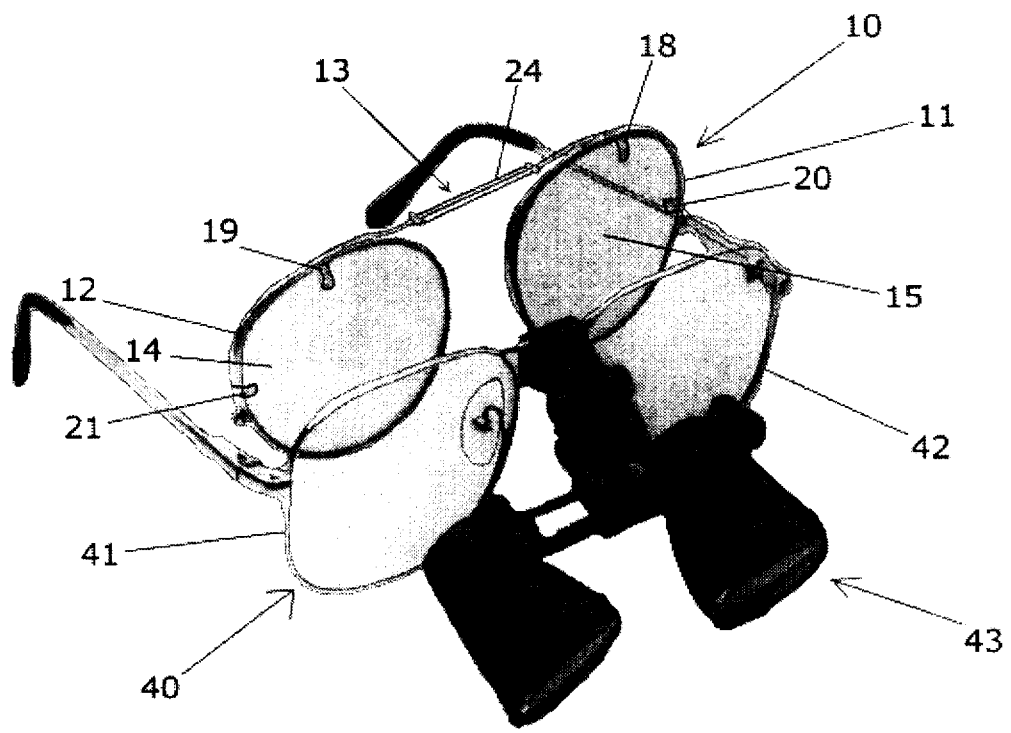
FIG. 2 is a perspective view also showing the clip-in laser eyewear assembly positioned for securement to another style of eyeglasses with magnifying loupes.

As shown in FIGS. 1 and 2, various styles of eyeglasses with magnifying loupes are utilized by physicians and dentists, for example. The clip-in laser eyewear assembly 10 of the present invention is shown positioned for securement to two styles of such eyeglasses with magnifying loupes, namely, eyeglass frame 30 having loupes 33 and 34 and eyeglass frame 40 having magnifying loupes 43.

As shown, the clip-in laser eyewear assembly 10 has a frame structure having a pair of laser filter lenses 14 and 15 that are held in place by lens frame members 11 and 12 and which are joined by an adjustable brow bar structure 13 having a spring member 24. Each lens frame member 11 and 12 is shown to have a clip 18 and 19 attached at the top and one on the outside edge 20 and 21 of the filter lens frame members 11 and 12. As shown, the top and side clips 18, 19, 20 and 21 are fixed generally to the upper and outer quadrant of each lens frame member 11 and 12; a quadrant being defined by a horizontal and vertical axis through each lens frame member. An upper and outer quadrant 29 is shown in FIG. 3 by horizontal axis "x" and vertical axis "y".

Each clip 18, 19, 20 and 21 is shown to have a hooked configuration whereby the length of the clip extends along the thickness of the eyeglass frame 31, 32 or 41, 42 and the terminal hook of the clip extends outwardly and spaced from the front of the eyeglass frame to thereby securely grasp the eyeglass frame. The frame structure of the assembly 10 is preferably constructed of a gold plated metal, for example, and the clips are fixed; i.e., by welding or other bonding means, to the filter lens frame. Preferably each clip has a plastic surface, for example, being coated with a plastic or like coating to prevent scratching and to provide a cushioned and secure attachment of the clip-in eyewear assembly 10 to the eyeglass frame 30 or 40.

Figure 3:
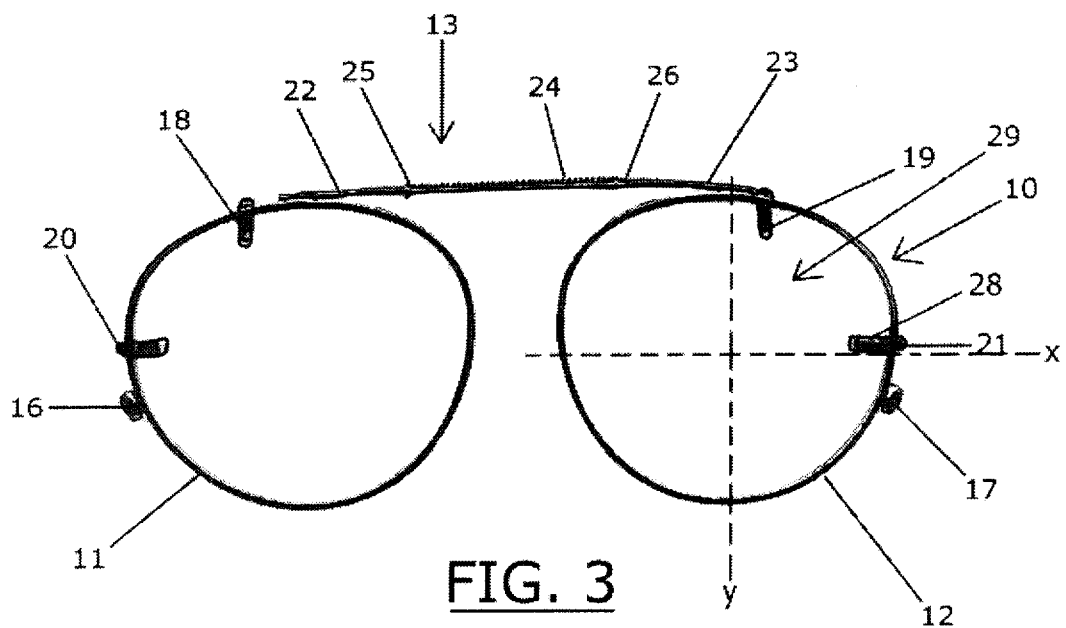
FIG. 3 is a rear view of the adjustable brow bar of the clip-in laser eyewear of the invention.

FIG. 3 further shows each lens frame member 11 and 12 having a frame/lens securement means 16 and 17 which is comprised of a structure that is mounted to each end of the split lens frame members 11 and 12. A screw is provided to fit the internally threaded structure so that after a laser filter lens is positioned in the lens frame member the screw is tightened to secure the filter lens in the frame.

Figure 4:
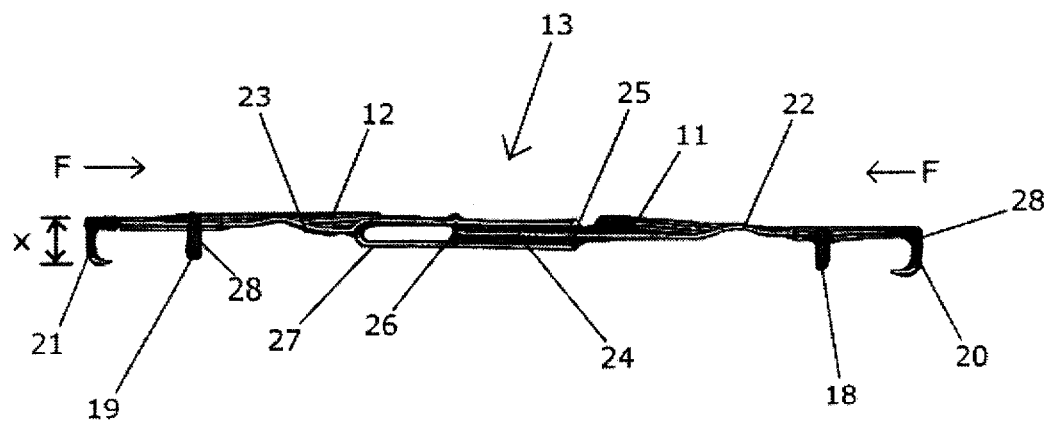
FIG. 4 is a top view of the adjustable brow bar of FIG. 3 and showing the spring member in a compressed state.

As further shown in FIGS. 3 and 4, the adjustable brow bar structure 13 has a spring member 24 which biases the filter lens frame members 11 and 12 towards each other as they are separated or pulled apart for securement to the eyeglasses. Consequently, as the clip-in laser eyewear assembly 10 is pulled outward to extend the distance separating the filter lens frame members 11 and 12 and the respective clips 18, 19, 20 and 21 are positioned against the top and sides of the eyeglasses with magnifying loupes, the clip-in laser eyewear assembly 10 is held in place on the inside of the eyeglasses by means of the cooperation of the respective top clips 18 and 19, the exterior clips 20 and 21 and the internally directed force of the spring member 24 of the adjustable brow bar structure 13. The internally directed forces are shown and marked as "F" in FIG. 4.

Referring particularly to FIGS. 3 and 4, the adjustable brow bar structure 13 of the clip-in laser eyewear assembly 10 is shown. The brow bar structure 13 at the top of the clip-in laser eyewear assembly 10 is shown comprised of opposing connecting members 22 and 23 that are fixed, i.e., welded, to the respective lens frame members 11 and 12 of the clip-in laser eyewear assembly 10. Each connecting member 22 and 23 is shown to have a bend to axially align the brow bar structure 13 with respect to the laser eyewear frame. The connecting structure 24 is shown to be elongated and has a terminal stop member 26 with two apertures. The spring member 24 is shown to be positioned about the elongated connecting structure and abuts the stop member 26. The other connecting structure 23 is shown to have a U-shaped or forked configuration member 27 having a terminal stop member 25 having one aperture therethrough. Thus, the spring member 24 is captured between the respective stop members 25 and 26 and the stop members with apertures permit the connecting members 22 and 23 to slide or move with respect to each other as the lens frame members 11 and 12 are separated from each other, thereby, compressing the spring member 24, and causing the side clip members 20 and 21 to have a biasing force to hold the clip-in eyewear assembly 10 to the eyeglasses. As particularly shown in FIG. 4, the top and side clip members 18, 19, 20 and 21 are generally L-shaped in configuration and the terminal legs are spaced a distance "x" from the frame member to accommodate the thickness of the eyeglass frame to which the clip-in assembly 10 is to be mounted.

In use, the clip-in laser eyewear assembly 10 is provided with filter lenses 14 and 15 designed for use with a particular laser source. The clip-in eyewear assembly 10 is pulled outwardly, thereby compressing the spring member 24 and adjust the brow bar structure 13, and the respective top and side clips 18, 19 and 20, 21 are positioned against the inside of the eyeglasses with magnifying loupes 30 or 40. The top clips 18 and 19 of the clip-in eyewear assembly 10 position the eyewear assembly with respect to the top of the eyeglass frames 30 and 40 while the outside clips 20 and 21 position the eyewear with respect to the outside of the eyeglass frames. Importantly, the spring 24 of the adjustable brow bar structure 13 provides an inwardly directed force which secures the clip-in eyewear assembly 10 to the inside of the eyewear frames.

The clip-in laser eyewear assembly 10 of the invention may be provided in several sizes (i.e., three sizes, small, medium and large) to accommodate a variety of eyeglass sizes. Each eyewear assembly size has different sized filter lenses to accommodate a particular lens size of the eyeglasses and to provide maximum protection to the user.

As many changes are possible to the embodiments of this invention utilizing the teachings thereof, the descriptions above and the accompanying drawings should be interpreted in the illustrative and not in the limited sense.

That which is claimed is:

1. A clip-in laser eyewear assembly for securement to the inside of a pair of eyeglasses comprising:
   a) a frame having two lens frame members, each said lens frame member having a top, an outer side, a front and a rear, each said lens frame member further being divided into four quadrants to thereby define an upper and outer quadrant lens frame portion;
   b) an adjustable brow bar structure having opposing ends, one said end connected to each said lens frame member, said brow bar structure having an internally directed force means for pulling said lens frames towards each other;
   c) a single hooked top clip member fixed to the top of each said lens frame member and extending outwardly to the front thereof within said upper and outer quadrant of each lens frame member, each said top clip member having a protective outer layer;
   d) a single hooked side clip member fixed to said outer side of each said lens frame member within said upper and outer quadrant lens frame member and extending outwardly to the front thereof each said side clip members having a protective outer layer, whereby the placement of said outwardly extending hooked top clips and said outwardly extending hooked side clips onto the inside of a pair of eyeglasses causes said clip-in laser eyewear assembly to be secured thereto by means of said internally directed force means of said adjustable brow bar structure; and
   e) a laser filter lens mounted in each said lens frame member, each said laser filter lens being constructed and arranged for filtering Diode, Erbium, YAG, Argon, KTP, Ruby and Alexandrite source laser beams.

2. The clip-in laser eyewear assembly of claim 1, wherein said force means of said brow bar structure is a spring.

3. The clip-in laser eyewear assembly of claim 1, wherein said top and side clips have an outwardly extending portion and an inwardly extending portion.

4. The clip-in laser eyewear assembly of claim 3, wherein said outwardly extending portion is equal to or greater than the thickness of the pair of eyeglasses to which it is attached.

5. The clip-in laser eyewear assembly of claim 3, wherein said protective layer of each said top and side clips are coated plastic layers.

6. The clip-in laser eyewear assembly of claim 1, wherein said frame is constructed of a metallic material and is plated.

7. The clip-in laser eyewear assembly of claim 6, wherein said top and side clips are welded to said frame.

8. The clip-in laser eyewear assembly of claim 1, wherein each said frame lens member is bifurcated and has securement means.

9. A clip-in laser eyewear assembly for the adjustable securement to the inside of a pair of eyeglasses comprising:
   a) a frame structure having a pair of lens frame members holding a pair of laser filter lenses, said laser filter lenses being constructed and arranged to filter Diode, Erbium, YAG, Argon, KTP, Ruby and Alexandrite source laser beams, each said lens frame member further having a front portion, a top portion, an outer side portion and an upper, outer quadrant;

b) an adjustable brow bar structure connecting said pair of lens frame members, said brow bar structure having biasing means to provide an inwardly directed force to bring said lens frame members towards each other when separated;

c) a plastic coated L-shaped top clip member extending outwardly from each said lens frame member and being fixed to the top of each said lens frame member generally within said upper, outer quadrant; and d) a plastic coated L-shaped side clip member extending outwardly from each said lens frame member and being fixed to the outer side portion of each said lens frame member generally within said upper outer quadrant, whereby the cooperation of the top clip members, the side clip members and the biasing means of said adjustable brow bar structure secure said clip-in laser eyewear assembly to the inside of a pair of eyeglasses.

10. The clip-in laser eyewear assembly of claim 9, wherein said biasing means is a spring member and wherein said brow bar structure further comprises cooperating sliding members constructed and arranged to constrain and compress said spring member.

11. The clip-in laser eyewear assembly of claim 9, wherein each said frame lens member is bifurcated and has securement means.

12. The clip-in laser eyewear assembly of claim 9, wherein said frame is constructed of a metallic material and is plated.

13. The clip-in laser eyewear assembly of claim 9, wherein said top and side clip members are welded to said frame structure.

14. A clip-in laser eyewear assembly for securement to the inside of a pair of eyeglasses with loupes comprising:

a) a frame having two lens frame members, each said lens frame member having a top, an outer side, a front and a rear, each said lens frame member further being divided into four quadrants to thereby define an upper and outer quadrant lens frame portion;

b) a laser filter lens mounted in each said lens frame member, each said laser filter lens being constructed and arranged for filtering Diode, Erbium, YAG, Argon, KTP, Ruby and Alexandrite source laser beams;

c) a spring loaded adjustable brow bar structure having opposing ends, one said end connected to each said lens frame member, said brow bar structure having an internally directed spring force for pulling said lens frames towards each other; and d) a single hooked top clip member fixed to the top of each lens frame member and extending outwardly to the front thereof within said upper and outer quadrant of each lens frame member, each said top clip member having a protective outer layer, and a single hooked side clip member fixed to said outer side of each said lens frame member within said upper and outer quadrant lens frame member and extending outwardly to the front thereof each said side clip members having a protective outer layer, whereby the placement of said outwardly extending hooked top clips and said outwardly extending hooked side clips onto the inside of a pair of eyeglasses causes said clip-in laser eyewear assembly to be secured thereto by means of said internally directed spring force means of said adjustable brow bar structure.

15. The clip-in laser eyewear assembly of claim 14, wherein said frame is constructed of a metallic material and is plated.

16. The clip-in laser eyewear assembly of claim 14, wherein said top and side clip members are welded to said frame structure.

* * * * *